US010369158B2

(12) United States Patent
Voskuhl

(10) Patent No.: US 10,369,158 B2
(45) Date of Patent: *Aug. 6, 2019

(54) PHARMACEUTICAL PACKAGING FOR ESTRIOL THERAPY

(71) Applicant: The Regents of the University of California, Oakland, CA (US)

(72) Inventor: Rhonda R. Voskuhl, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/307,198

(22) PCT Filed: Apr. 27, 2015

(86) PCT No.: PCT/US2015/027756
§ 371 (c)(1),
(2) Date: Oct. 27, 2016

(87) PCT Pub. No.: WO2015/168002
PCT Pub. Date: Nov. 5, 2015

(65) Prior Publication Data
US 2017/0042910 A1 Feb. 16, 2017

Related U.S. Application Data

(60) Provisional application No. 62/032,944, filed on Aug. 4, 2014, provisional application No. 61/985,184, filed on Apr. 28, 2014, provisional application No. 61/985,380, filed on Apr. 28, 2014.

(51) Int. Cl.
*A61K 31/566* (2006.01)
*A61K 31/57* (2006.01)
*A61K 9/00* (2006.01)
*A61K 45/06* (2006.01)

(52) U.S. Cl.
CPC .......... *A61K 31/566* (2013.01); *A61K 9/0053* (2013.01); *A61K 31/57* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,932,635 A * | 1/1976 | Segre | A61K 31/565 514/170 |
| 4,826,831 A | 5/1989 | Plunkett et al. | |
| 5,108,995 A | 4/1992 | Casper | |
| 9,962,395 B2 | 5/2018 | Voskuhl | |
| 2005/0113350 A1 | 5/2005 | Duesterberg et al. | |
| 2005/0239758 A1 | 10/2005 | Roby | |
| 2009/0005351 A1 | 1/2009 | Pickar et al. | |
| 2010/0168071 A1 * | 7/2010 | Boissonneault | A61K 31/565 514/170 |
| 2010/0203016 A1 | 8/2010 | Voskuhl | |
| 2012/0282222 A9 | 11/2012 | Voskuhl et al. | |
| 2013/0203722 A1 | 8/2013 | Voskuhl | |
| 2017/0049785 A1 | 2/2017 | Voskuhl | |
| 2017/0290845 A1 | 10/2017 | Voskuhl | |

FOREIGN PATENT DOCUMENTS

| | | |
|---|---|---|
| AU | 2004257772 A1 | 1/2005 |
| WO | WO-01070208 A2 | 9/2001 |
| WO | WO-2002/085364 A1 | 10/2002 |
| WO | WO-2002/085374 | 10/2002 |
| WO | WO-2002/092102 A2 | 11/2002 |
| WO | WO-2002/092102 A3 | 11/2002 |
| WO | WO-2007/038435 A2 | 4/2007 |
| WO | WO-2007/038636 A2 | 4/2007 |
| WO | WO-2008/150547 A1 | 12/2008 |
| WO | WO-2010/050916 A1 | 5/2010 |
| WO | WO-2015/168000 A1 | 11/2015 |

OTHER PUBLICATIONS

Holtorf et al. Postgraduate Medicine 121(1) (2009) (Year: 2009).*
Sicotte et al. in Ann Neurol 52(4): 421-428 (2002) (Year: 2002).*
Gold et al., "Estrogen treatment in multiple sclerosis," J Neurol Sci, 286(1-2):99-103 (2009).
International Search Report of the International Searching Authority, dated Aug. 3, 2015, from related International Application No. PCT/US2015/027756.
International Search Report of the International Searching Authority, dated Aug. 5, 2015, from related International Application No. PCT/US2015/027752.
International Search Report of the International Searching Authority, dated Jan. 10, 2016, from related International Application No. PCT/US2015/047906.
International Search Report of the International Searching Authority, dated Dec. 24, 2015, from related International Application No. PCT/US2015/052805.
International Search Report of the International Searching Authority, dated Feb. 16, 2016, from related International Application No. PCT/US2015/056649.
International Search Report of the International Searching Authority, dated Jul. 11, 2016, from related International Application No. PCT/US2016/024754.
International Search Report of the International Searching Authority, dated Jul. 21, 2016, from related International Application No. PCT/US2016/024751.
MacKenzie-Graham et al., "Estrogen treatment prevents gray matter atrophy in experimental autoimmune encephalomyelitis," J Neurosci Res, 90(7):1310-23 (2012).
Prempro and Premphase drug information, Food and Drug Administration, dated Jun. 5, 2003, Retrieved from the Internet. URL: http://www.fda.gov/ohrms/dockets/ac/03/briefing/39921B1_03_FDA-Prempro-Premphase.pdf.

(Continued)

*Primary Examiner* — Dennis Heyer
(74) *Attorney, Agent, or Firm* — Foley Hoag LLP; David P. Halstead, J.D.; Alexander J. Chatterley

(57) ABSTRACT

This invention relates to novel packaged pharmaceutical products for the treatment of neurodegenerative diseases, such as multiple sclerosis, and methods of using these products.

20 Claims, 7 Drawing Sheets

(56) References Cited

OTHER PUBLICATIONS

Smith et al., "Impact of combined estradiol and norethindrone therapy on visuospatial working memory assessed by functional magnetic resonance imaging," J Clin Endocrinol Metab, 91(11):4476-81 (2006).
Speroff et al., "Postmenopausal hormone therapy," Gynecololgy and Obstetrics, Chapter 110, Mar. 8, 2011. URL: http://www.glowm.com/resources/glowm/cd/pages/v1/v1c110.html.
Alhola et al., "Estrogen+ progestin therapy and cognition: A randomized placebo controlled double blind study," J Obstet Gynaecol Re, 36(4): 796-802 (2010).
Anderer et al., "Age-related cognitive decline in the menopause: effects of hormone replacement therapy on cognitive event-related potentials," Maturitas, 51(3): 254-269 (2005).
Luchetti et al., "Gender Differences in Multiple Sclerosis: Induction of Estrogen Signaling in Male and Progesterone Signaling in Female Lesions," J Neuropathol Exp Neurol, 73(2): 123-135 (2014).
Nicot, "Gender and sex hormones in multiple sclerosis pathology and therapy," Front Biosci (Landmark Ed), 14: 4477-4515 (2009).
Sicotte et al., "Treatment of Multiple Sclerosis with the Pregnancy Hormone Estriol," Ann Neurol, 52(4): 421-428 (2002).
Anderson, "Adding estriol reduces ms relapse rate," Medscape Medical News, pp. 1-4 (2014). [https://www.medscape.com/viewarticle/824364].
Anonymous: "Estriol Treatment in Multiple Sclerosis (MS): Effect on Cognition," ClinicalTrials.gov archive, pp. 1-5 (2013). NCT01466114.
Extended European Search Report issued by the European Patent Office in corresponding Application No. 15846358.8, dated Apr. 17, 2018.
Extended European Search Report issued by the European Patent Office in corresponding Application No. EP 15786314.3, dated Dec. 1, 2017.
Extended European Search Report issued by the European Patent Office in corresponding Application No. EP 15786637.7, dated Dec. 1, 2017.
Itoh et al., "Bedside to bench to bedside research: Estrogen receptor beta ligand as a candidate neuroprotective treatment for multiple sclerosis," J Neuroimmunol, 304:63-71 (2017).
Kipp et al., "Multiple sclerosis: neuroprotective alliance of estrogen-progesterone and gender," Front Neuroendocrin, 33(1):1-16 (2012).
Luine, "Estradiol and cognitive function: past, present and future," Horm Behav, 66(4):602-618 (2014).
Soldan et al., "Immune modulation in multiple sclerosis patients treated with the pregnancy hormone estriol," J Immunol, 171(11):6267-6274 (2003).
Spence et al., "Neuroprotective effects of estrogens and androgens in CNS inflammation and neurodegeneration," Front Neuroendocrinol, 33(1):105-115 (2012).
Voskuhl et al., "Estriol combined with glatiramer acetate for women with relapsing-remitting multiple sclerosis: a randomised, placebo-controlled, phase 2 trial," Lancet Neurol, 15(1):35-46 (2016).
Zhang et al., "Distribution and differences of estrogen receptor beta immunoreactivity in the brain of adult male and female rats," Brain Res, 935(1-2):73-80 (2002).
Tiwari-Woodruff et al., "Neuroprotective and anti-inflammatory effects of estrogen receptor ligand treatment in mice," Journal of Neurological Sciences, 286:81-85 (2009).
Blasco et al., "Amyotrophic Lateral Sclerosis," Informa Healthcare, 13:585-588 (2012).
Chen et al., "The Treatment Strategies for Neurodegenerative Diseases by Integrative Medicine," Integrative Medicine International, 1:223-225 (2014).
Cubo et al., "Effect of Donepezil on Motor and Cognitive Function in Huntington Disease," Neurology, 67(7):1268-1271 (2006).
Extended European Search Report issued by the European Patent Office in corresponding Application No. PCT/US2016/024754 dated Nov. 21, 2018.
MacKenzie-Graham et al., "Estriol-mediated neuroprotection in multiple sclerosis localized by voxel-based morphometry." Brain and behavior: e01086 (2010).
Nicot, "Gender and sex hormones in multiple sclerosis pathology and therapy," Front Biosci, 14:4477-4515 (2009).
Reed et al., "The Normal Menstrual Cycle and the Control of Ovulation," Europepmc.ord, 1-26 (2018).
Rubin, "Parkinson's Disease in Women," American Parkinson Disease Association, https://www.apdaparkinson.org/parkinsons-disease-in-women/ (2015).
Schiff et al., "Effect of Estriol Administration on the Hypogonadal Woman," Fertility and Sterility, 30(3):278-282 (1978).
Schiff et al., "Plasma estriol and its conjugates following oral and vaginal administration of estriol to postmenopausal women: Correlations with gonadotropin levels," Am J Obstet Gynecol, 138(8):1137-1141 (1980).
Rosti et al., "The PASAT performance among patients with multiple sclerosis: analyses of responding patterns using different scoring methods," Multiple Sclerosis, 12:586-593 (2006).
Bendfeldt et al., "Effect of immunomodulatory medication on regional gray matter loss in relapsing-remitting multiple sclerosis—A longitudinal MRI study," Brain Research, 1325:174-182 (2010).
Geurts et al., "Measurement and clinical effect of grey matter pathology in multiple sclerosis," Lancet Neurol, 11:1082-1092 (2012).
Lanka et al., "Therapy development for ALS: Lessons learned and path forward," Amyotrophic Lateral Sclerosis, 9:131-140 (2008).
Mayo Clinic, "Huntington's Disease," https:mayoclinic.org/diseases-conditions/huntingtons-disease/symptoms-causes/syc-20356117?p=1 (2008).
Ransohoff et al., "Animal models of multiple sclerosis: the good, the bad and the bottom line," Nature Neuroscience, 15:1074-1077 (2012).
Tolppanen et al., "Systemic Estrogen Use and Discontinuation After Alzheimer's disease Diagnosis in Finland 2005-2012: A Nationwide Exposure-Matched Cohort Study," Drugs & Aging, 35:985-992 (2018).
Vickers, "A Vaccine Against Alzheimer's Disease," Drugs Aging, 19:487-494 (2002).
Zivadinov et al., "Interferon beta-1a slows progression of atrophy in relapsing-remitting multiple sclerosis predominantly by reducing gray matter atrophy," Multiple Sclerosis, 13:490-501 (2007).

* cited by examiner

Estriol plus Copaxone

Placebo plus Copaxone

PHARMACEUTICAL PACKAGING FOR ESTRIOL THERAPY

PRIORITY CLAIM

This application is a § 371 national-stage application based on PCT Application PCT/US2015/027756, filed Apr. 27, 2015, which claims priority to U.S. Provisional Patent Application No. 61/985,184, filed on Apr. 28, 2014, U.S. Provisional Patent Application No. 61/985,380, filed on Apr. 28, 2014, and U.S. Provisional Patent Application No. 62/032,944, filed on Aug. 4, 2014, each of which is hereby incorporated by reference in its entirety.

STATEMENT OF GOVERNMENT SUPPORT

This invention was made with government support under Grant Number NS051591, awarded by the National Institutes of Health. The government has certain rights in the invention.

BACKGROUND

Multiple sclerosis (MS) is a chronic, often debilitating disease affecting the central nervous system (brain and spinal cord). MS affects more than 1 million people worldwide and is the most common neurological disease among young adults, particularly women.

The exact cause of MS is still unknown. MS is an autoimmune disease in which myelin sheaths surrounding neuronal axons are destroyed. Such neurodegeneration can cause weakness, impaired vision, loss of balance, and poor muscle coordination.

MS takes several forms, with new symptoms either occurring in isolated attacks (relapsing forms) or building up over time (progressive forms). Between attacks, symptoms may disappear completely; however, permanent neurological problems often occur, especially as the disease advances.

In 1996, the United States National Multiple Sclerosis Society described four clinical subtypes of MS: (i) relapsing-remitting; (ii) secondary-progressive; (iii) primary-progressive; and (iv) progressive-relapsing.

Relapsing-remitting MS is characterized by unpredictable relapses followed by periods of months to years of relative quiet (remission) with no new signs of disease activity. Deficits that occur during attacks may either resolve or leave sequalae, the latter in about 40% of attacks and being more common the longer a person has had the disease. This describes the initial course of 80% of individuals with MS. When deficits always resolve between attacks, this is sometimes referred to as benign MS, although people will still build up some degree of disability in the long term. On the other hand, the term malignant multiple sclerosis is used to describe people with MS having reached significant level of disability in a short period of time. The relapsing-remitting subtype usually begins with a clinically isolated syndrome (CIS). In CIS, a person has an attack suggestive of demyelination but does not fulfill the criteria for multiple sclerosis; 30 to 70% of persons experiencing CIS go on to develop MS.

Secondary-progressive MS occurs in around 65% of those with initial relapsing-remitting MS, who eventually have progressive neurologic decline between acute attacks without any definite periods of remission. Occasional relapses and minor remissions may appear. The median length of time between disease onset and conversion from relapsing-remitting to secondary progressive MS is 19 years.

Primary-progressive MS occurs in approximately 10-20% of individuals, with no remission after the initial symptoms. It is characterized by progression of disability from onset, with no, or only occasional and minor, remissions and improvements. The usual age of onset for the primary progressive subtype is later than of the relapsing-remitting subtype, but similar to the age that secondary-progressive MS usually begins in relapsing-remitting MS, around 40 years of age.

Progressive-relapsing MS describes those individuals who, from onset, have a steady neurologic decline but also have clear superimposed attacks. This is the least common of all subtypes.

Currently the following agents are approved by the U.S. Food and Drug Administration (FDA) to reduce disease activity and disease progression for many people with relapsing forms of MS, including relapsing-remitting MS, as well as secondary-progressive and progressive-relapsing MS in those people who continue to have relapses: dimethyl fumarate (Tecfidera®; BG-12), fingolimod (Gilenya®), glatiramer acetate (Copaxone®), interferon beta-1a (Avonex® and Rebif®), interferon beta-1b (Betaseron® and Extavia®), mitoxantrone (Novantrone®), natalizumab (Tysabri®), and teriflunomide (Aubagio®). However, many of these therapies fail to successfully treat all patients or all symptoms in treated patients, and many of these therapies are associated with undesirable side effects.

Furthermore, MS treatment may require detailed treatment regimens to provide adequate therapy and minimize undesirable side effects. Such regimens, when administered by the patient, often suffer from issues of patient compliance/adherence. Accordingly, reproducible treatment protocols and pharmaceutical packaging to facilitate patient compliance are needed.

SUMMARY

The present invention provides, inter alia, effective treatments for neurodegenerative diseases, such as multiple sclerosis, that reduce the risk of side effects relative to prior art therapies. Further, the present invention provides, inter alia, packaging designed to increase patient compliance with the treatment regime, in order to maximize the benefit and minimize the side effects of the treatment regime. In some aspects, the invention relates to a packaged pharmaceutical product, comprising a first region comprising a first series of doses of an estrogen, wherein each dose of the estrogen is associated with (e.g., adjacent or proximal to, or even co-located with) a dose of a progestogen; and a second region comprising a second series of doses of the estrogen that are not associated with doses of the progestogen. In such embodiments, the first region comprises both (i) a first series of doses of an estrogen and (ii) each dose of the progestogen with which the doses of estrogen are associated. In some embodiments, each dose of the estrogen in the second region is associated with a dose of placebo. In such embodiments, the second region comprises both (i) a second series of doses of an estrogen and (ii) each dose of the placebo with which the doses of estrogen are associated, such as in the manner that the doses of estrogen in the first series are associated with doses of the progestogen.

In certain aspects, the invention relates to a method of using a packaged pharmaceutical product, comprising ingesting one dose of an estrogen and one dose of a progestogen daily from a first region of the product, and when the doses in the first region are exhausted, ingesting one dose of estrogen daily from a second region of the product. In some embodiments, when the doses in the first region are exhausted, the method comprises ingesting one dose of the placebo daily from the second region of the product with each dose of the estrogen from the second series with which the dose of the placebo is associated.

In some aspects, the invention relates to a packaged pharmaceutical product comprising a first region comprising a first series of doses of an estrogen, wherein each dose of the estrogen comprises a dose equal or equivalent to about 4 mg of estriol, and a second region comprising a second series of doses of the estrogen, wherein each dose of the estrogen comprises a dose equal or equivalent to about 2 mg of estriol.

In certain aspects, the invention relates to a method of using a packaged pharmaceutical product comprising ingesting one dose of an estrogen daily from a first region of the product, and when the doses from the first region are exhausted, ingesting one dose of the estrogen daily from a second region of the product.

DETAILED DESCRIPTION

Approximately 50% of people diagnosed with multiple sclerosis (MS) will develop problems with cognition. Currently, there are no FDA-approved treatments targeting cognitive function in MS. Multiple sclerosis relapses are known to be significantly decreased by approximately 80% during late pregnancy. This disease improvement may be due to estriol, an estrogen unique to pregnancy, or one or more as-yet-unidentified factors. Estriol blood levels go from undetectable levels prior to pregnancy, increase during pregnancy and reach highest levels during late pregnancy. Further, estrogen treatment has been shown to have favorable effects on cognition in animal models of other neurological diseases. The additional use of a progestogen can offset some of the side-effects of estrogen therapy.

Figure 6A:
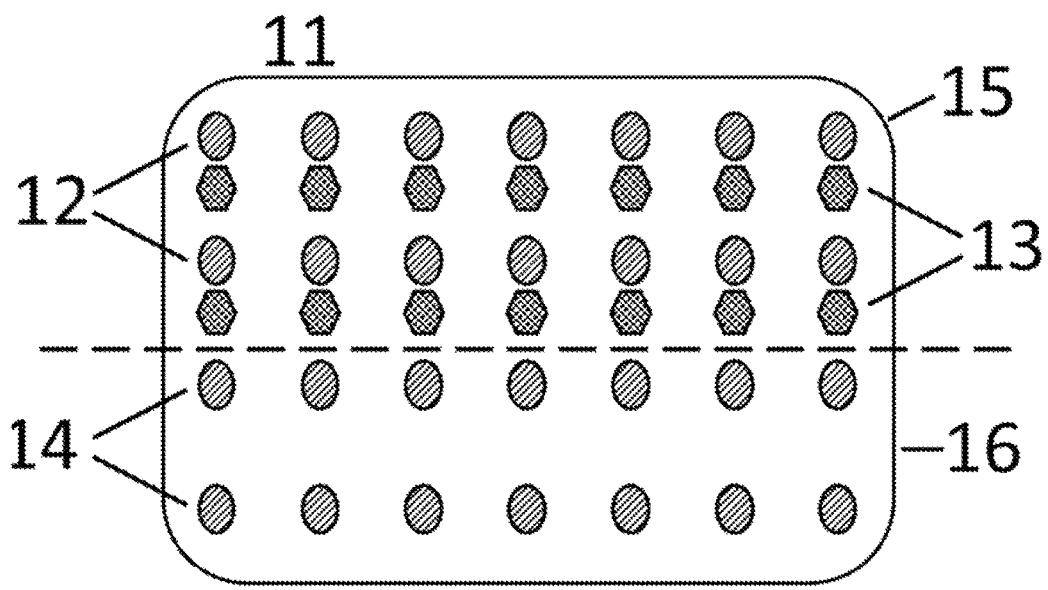
FIG. 6 depicts an embodiment of the packaged pharmaceutical product described herein, comprising a first support structure 11; a first region 15 comprising a first series of doses of an estrogen 12 and each dose of progestogen with which the first series of doses of estrogen are associated 13; a second region 16 comprising a second series of doses of the estrogen 14; and a second support structure 17.

In some aspects, the invention relates to novel packaged pharmaceutical products for the treatment of neurodegenerative diseases, such as multiple sclerosis. FIG. 6 depicts an embodiment of the packaged pharmaceutical product described herein, comprising a first support structure 11 and a second support structure 17. The first support structure 1 comprises a first region 15 comprising a first series of fourteen doses of estrogen 12, and each dose of the estrogen is associated with a dose of a progestogen 13.

Figure 6B:
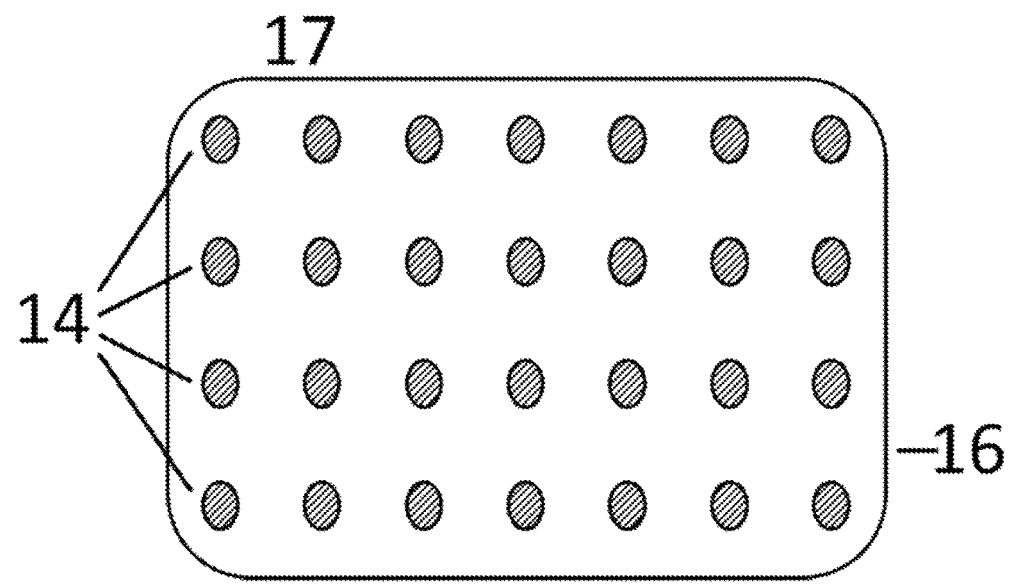

The first support structure 11 also comprises a portion of the second region 16, wherein the second region comprises a second series of doses of estrogen 14. Additionally, the second support structure 17 comprises a portion of the second region 16. As depicted in FIG. 6, the entire second region, over both support structures, comprises at least forty-two doses of estrogen. FIG. 6 depicts that fourteen doses of estrogen from the second region 16 are held by the first support structure 11 and twenty-eight doses of estrogen from the second region 16 are held by the second support structure 17. In preferred embodiments, the product comprises a third support structure identical to the second support structure 17 depicted in FIG. 6B, to provide an additional twenty-eight doses of estrogen from the second region 16, such that the second region 16, over all three support structures, comprises seventy total doses of the estrogen, in accordance with embodiments disclosed herein where the administration cycle is 84 days. In certain embodiments, such as where the product provides sufficient doses for two or more administration cycles, the product may comprise multiple sets of support structures as described above, one set for each administration cycle.

The first support structure 11 comprises a first grid that consists of seven columns and four rows. The first series of doses of the estrogen 12, each with its associated dose of progesterone 13, constitutes the first two rows. The use of seven columns permits the user to easily associate each column with a day of the week, in analogy with a calendar.

The intersection of a row and a column defines a position for locating one or two chambers. In certain embodiments, each position in the first and second rows of the first support structure 11 comprises two chambers, wherein one dose of the estrogen from the first series 12 occupies a first chamber at each position and its associated dose of the progestogen occupies a second chamber at each position. Preferably, though, each position in the first and second rows comprises a single chamber that holds both the dose of estrogen and the dose of progestogen. Each position in the third and fourth rows of the first support structure 11 comprises one chamber, wherein one dose of the estrogen from the second series 14 occupies the chamber at each position. Each position in the second support structure 17 comprises one chamber, wherein one dose of the estrogen from the second series 14 occupies the chamber at each position.

Figure 7A:
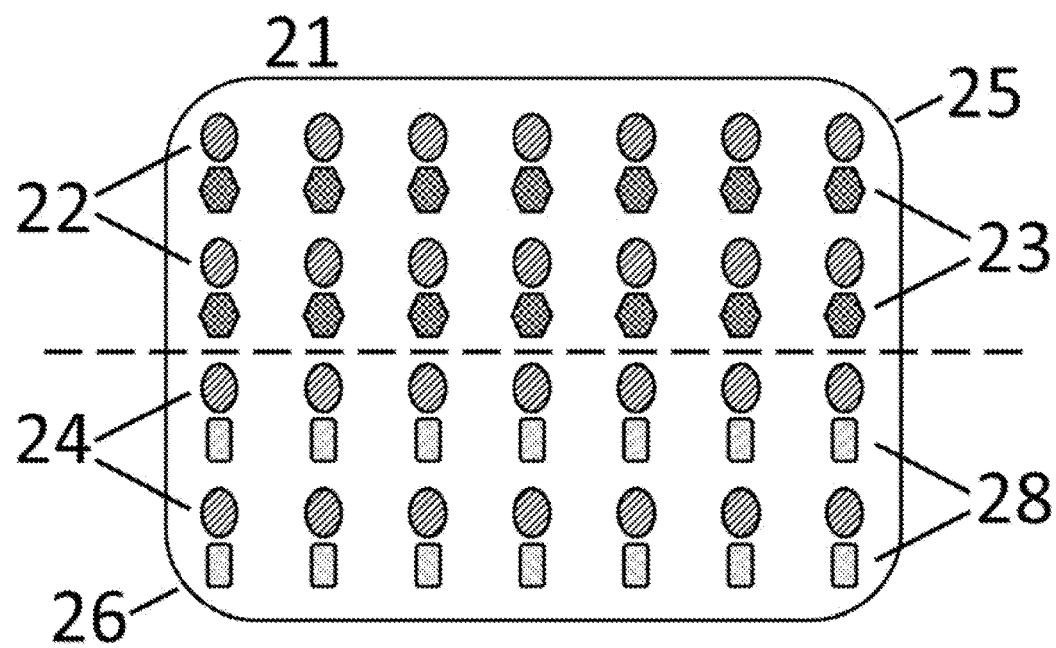
FIG. 7 depicts an embodiment of the packaged pharmaceutical product described herein, comprising a first support structure 21; a first region 25 comprising a first series of doses of an estrogen 22 and each dose of progestogen with which the first series of doses of estrogen are associated 23; a second region 26 comprising a second series of doses of the estrogen 24 and each dose of placebo with which the second series of doses of estrogen are associated 28; and a second support structure 27.
Figure 7B:
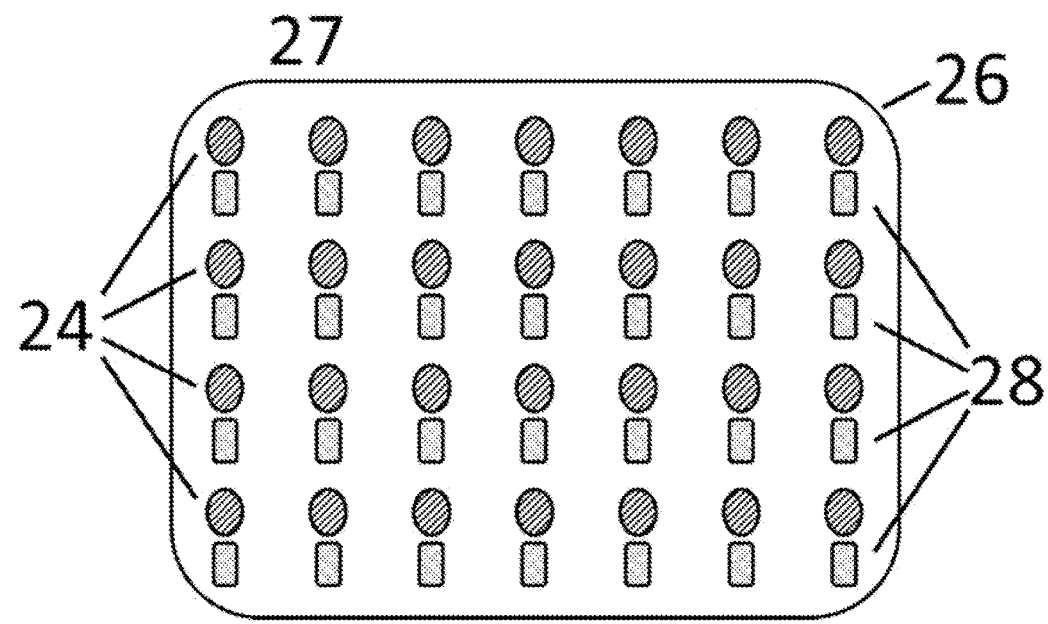

FIG. 7 depicts an embodiment of the packaged pharmaceutical product described herein, comprising a first support structure 21 and a second support structure 27. The first support structure 21 comprises a first region 25 comprising a first series of fourteen doses of estrogen 22, and each dose of the estrogen is associated with a dose of a progestogen 23.

The first support structure 21 also comprises a portion of the second region 26, wherein the second region comprises a second series of doses of estrogen 24, and each dose of the estrogen is associated with a dose of a placebo 28. Additionally, the second support structure 27 comprises a portion of the second region 26. As depicted in FIG. 7, the entire second region, over both support structures, comprises at least forty-two doses of estrogen and forty-two doses of placebo. FIG. 7 depicts that fourteen doses each of estrogen and placebo from the second series 24 are held by the first support structure 21 and twenty-eight doses each of estrogen and placebo from the second series 24 are held by the second support structure 27. In preferred embodiments, the product comprises a third support structure identical to the second support structure 27 depicted in FIG. 78, to provide an additional twenty-eight doses each of estrogen and placebo from the second series 24, such that the second region 26, over all three support structures, comprises seventy total doses each of the estrogen and the placebo, in accordance with embodiments disclosed herein where the administration cycle is 84 days. In certain embodiments, such as where the product provides sufficient doses for two or more administration cycles, the product may comprise multiple sets of support structures as described above, one set for each administration cycle.

The first support structure 21 comprises a first grid that consists of seven columns and four rows. The first series of doses of the estrogen 22, each with its associated dose of progesterone 23, constitutes the first two rows. The use of seven columns permits the user to easily associate each column with a day of the week, in analogy with a calendar.

The intersection of a row and a column defines a position for locating one or two chambers. In certain embodiments, each position in the first and second rows of the first support structure 21 comprises two chambers, wherein one dose of the estrogen from the first region 22 occupies a first chamber at each position and one dose of the progestogen from the first region 22 occupies a second chamber at each position. Preferably, though, each position in the first and second rows comprises a single chamber that holds both the dose of estrogen and the dose of progestogen. In certain embodiments, each position in the third and fourth rows of the first support structure 21 and each position in the second support structure 27 comprise two chambers, wherein one dose of the estrogen from the second region 26 occupies a first chamber at each position and one dose of the placebo from the second region 26 occupies a second chamber at each position. Preferably, though, each position in the third and fourth rows of the first support structure and each position in the second (and, if present, third) support structure 27 comprise a single chamber that holds both the dose of estrogen and the dose of placebo.

Definitions

The term "estrogen" as used herein refers to any biologically active form of estrogen or precursor thereof. The term "estrogen" thus embraces naturally occurring, synthetic, and semi-synthetic forms of estrogen, and biologically active, pharmaceutically acceptable salts and esters thereof.

In certain embodiments, the estrogen is one or more of estriol (E3), estradiol (E2), estrone (E1), an ester thereof, a pharmaceutically acceptable salt of an ester thereof, and any combination of the foregoing. In certain embodiments, estrogen is estriol (E3) or an ester thereof, or a pharmaceutically acceptable salt of an ester thereof. For example, the estrogen can be estriol, estriol succinate, estriol dihexanoate, or estriol sulfate.

In certain embodiments, the estrogen is formulated for oral administration, e.g., in a dose equal or equivalent to about 200 µg to about 20 mg estriol daily. For example, a dose of 2 to 4 mg of estriol is generally considered to be equivalent to 0.6 to 1.25 mg of conjugated estrogens or estrone. In certain embodiments, the estrogen is formulated for oral administration in a dose equal or equivalent to about 1 mg to about 10 mg estriol daily, preferably equal or equivalent to about 8 mg estriol daily. In most preferred embodiments, the estrogen is estriol formulated for oral administration in a dose of about 8 mg estriol daily.

The dosage of the estrogen may be selected for an individual patient depending upon the route of administration, severity of disease, age and weight of the patient, other medications the patient is taking and other factors normally considered by the attending physician, when determining the individual regimen and dosage level as the most appropriate for a particular patient.

The therapeutically effective dose of the estrogen included in the dosage form is selected at least by considering the type of estrogen selected and the mode of administration. The dosage form may include the estrogen in combination with other inert ingredients, including adjuvants and pharmaceutically acceptable carriers for the facilitation of dosage to the patient as known to those skilled in the pharmaceutical arts. The dosage form may be any form suitable to cause the estrogen to enter into the tissues of the patient.

In one embodiment, the dosage form of the estrogen is an oral preparation (liquid, tablet, capsule, caplet, or the like) which when consumed results in elevated serum estrogen levels. The oral preparation may comprise conventional carriers including diluents, binders, time-release agents, lubricants, and disintegrants.

In other embodiments of the invention, the dosage form of the estrogen may be provided in a topical preparation (lotion, cream, ointment, or the like) for transdermal application.

Alternatively, the dosage form may be provided as a suppository or the like for transvaginal or transrectal application.

However, in other embodiments, the dosage form may also allow for preparations to be applied subcutaneously, intravenously, intramuscularly, or via the respiratory system.

The term "progestogen" (also known as "gestagen") as used herein refers to any compound, typically a steroid hormone, that binds to and activates a progesterone receptor, or a precursor thereof. The term "progestogen" thus embraces naturally occurring, synthetic, and semi-synthetic forms of progestogen, and biologically active, pharmaceutically acceptable salts and esters thereof. In certain embodiments, the progestogen is selected from chlormadinone acetate, cyproterone acetate, desogestrel, dienogest, 5α-dihydroprogesterone, drospirenone (Yasmin®), ethynodiol diacetate, etonogestrel (Nexplanon®), gestodene, 17-hydroxyprogesterone, levonorgestrel (Alesse®), medroxyprogesterone acetate (17α-hydroxy-6α-methylprogesterone acetate; Provera®), megestrol megestrol acetate (17α-acetoxy-6-dehydro-6-methylprogesterone), nestorone, nomegestrol acetate, norethindrone (also known as norethisterone), norethindrone acetate (also known as norethisterone acetate), norethynodrel (Enovid®), norgestimate, norgestrel, progesterone, tanaproget, trimegestone, or a pharmaceutically acceptable salt of any of the foregoing, or any combination thereof.

In certain embodiments, the progestogen is selected from progesterone, 17-hydroxyprogesterone, 5α-dihydroprogesterone, norethindrone, norethindrone acetate, desogestrel, levonorgestrel, medroxyprogesterone acetate, megestrol, chlormadinone acetate, cyproterone acetate, norethynodrel, ethynodiol diacetate, norgestrel, gestodene, norgestimate, dienogest, drospirenone, etonogestrel, nestorone, nomegestrol acetate, trimegestone, and tanaproget, pharmaceutically acceptable salts and esters of any of the foregoing, and any combination thereof. In certain embodiments, progestogen is norethindrone or an ester thereof, or a pharmaceutically acceptable salt of an ester thereof, preferably norethindrone. In certain embodiments, progestogen is progesterone or an ester thereof, or a pharmaceutically acceptable salt of an ester thereof.

In certain embodiments, progestogen is a progestin. The term "progestin" as used herein refers to a synthetic progestogen as defined herein. Examples of progestins include desogestrel, dienogest, drospirenone (Yasmin®), ethinodiol diacetate, etonogestrel (Nexplanon®), gestodene, levonorgestrel (Alesse®), medroxyprogesterone acetate (Provera®), nestorone, nomegestrol acetate, norethindrone, norethindrone acetate, norethynodrel (Enovid®), norgestimate, norgestrel, and trimegestone.

In certain embodiments, the progestogen is formulated for oral administration, e.g., in a dose equal or equivalent to about 70 µg to about 7 mg norethindrone daily, such as about 100 µg to about 1 mg norethindrone daily, most preferably in a dose equal or equivalent to about 0.7 mg norethindrone daily. In certain preferred embodiments, the progestogen is norethindrone formulated for oral administration in a dose of 0.7 mg norethindrone daily.

The therapeutically effective dose of the progestogen included in the dosage form can be selected at least by considering the type of progestogen selected and the mode of administration. The dosage form may include the progestogen in combination with other inert ingredients, including adjuvants and pharmaceutically acceptable carriers for the facilitation of dosage to the patient as known to those skilled in the pharmaceutical arts. The dosage form may be any form suitable to cause the progestogen to enter into the tissues of the patient.

In one embodiment, the dosage form of the progestogen is an oral preparation (liquid, tablet, capsule, caplet, or the like) which when consumed results in elevated serum progestogen levels. The oral preparation may comprise conventional carriers including diluents, binders, time-release agents, lubricants, and disintegrants.

Alternatively, the dosage form may be provided as a suppository or the like for transvaginal or transrectal application.

In certain embodiments, the estrogen and the progestogen are formulated separately from one another, e.g., the subject receives the estrogen as a single formulation and the progestogen as a separate formulation. For oral administration, a given dose of each formulation can comprise one or more pills, tablets, capsules, or the like (i.e., unit doses). For example, an 8 mg dose of estriol can be administered as four 2 mg capsules, and a 0.7 mg dose (or about 1 mg) of norethindrone can be administered as a single capsule, though preferably each dose is administered in a single unit dose (e.g., one unit dose each for the estrogen and the progestogen).

In certain embodiments, e.g., where a placebo is administered with the estrogen on days when progestogen is not administered, the estrogen and the placebo are formulated separately from one another. For example, the subject is administered the estrogen as a single formulation and the placebo as a separate formulation. For oral administration, a given dose of each formulation can comprise one or more pills, tablets, capsules, or the like (i.e., unit doses). For example, an 8 mg dose of estriol can be administered as four 2 mg capsules, and a placebo can be administered as a single capsule.

When a given dose of any agent involves administration of more than a single unit dose, e.g., four 2 mg capsules of estriol, the individual unit doses can be administered at essentially the same time, or they can be administered at different times on a given day, provided the entire daily dose is administered within a single day. For example, four 2 mg capsules of estriol can be taken together essentially once a day, or they may be taken two at a time twice a day, or they may be taken one at a time four times a day. Additional schedules are contemplated by the invention, again provided the entire daily dose is administered within a single day. While it may be preferable that the subject follow the same schedule from one day to the next, such is not required, once again provided the entire daily dose is administered within a single day.

When the estrogen and the progestogen are formulated separately, they can be administered essentially simultaneously, or they can be administered sequentially with respect to each other. For example, in one embodiment the subject is administered four 2 mg capsules of estriol and one 0.7 mg (or about 1 mg) capsule of norethindrone essentially simultaneously. In another embodiment, the subject is administered estriol in divided doses, e.g., two 2 mg capsules twice daily, and the progestogen is administered essentially simultaneously with one of the divided doses of estriol. In yet another embodiment, the subject is administered estriol in divided doses, e.g., two 2 mg capsules twice daily, and the progestogen is administered at a separate time from either one of the divided doses of estriol.

Similarly, when the estrogen and the placebo are formulated separately, they can be administered essentially simultaneously, or they can be administered sequentially with respect to each other. For example, in one embodiment the subject is administered four 2 mg capsules of estriol and one placebo essentially simultaneously. In another embodiment, the subject is administered estriol in divided doses, e.g., two 2 mg capsules twice daily, and the placebo is administered essentially simultaneously with one of the divided doses of estriol. In yet another embodiment, the subject is administered estriol in divided doses, e.g., two 2 mg capsules twice daily, and the placebo is administered at a separate time from either one of the divided doses of estriol.

In certain embodiments, the estrogen and the progestogen are formulated together. For oral administration, a given dose of each component, formulated together, can comprise one or more pills, tablets, capsules, or the like (i.e., unit doses). For example, an 8 mg dose of estriol and a 0.7 mg dose of norethindrone can be coformulated and administered as four capsules, each containing 2 mg estriol and 0.0875 mg (or about 100 µg, or about 90 µg, or about 80 µg, or about 70 µg) norethindrone, though preferably, where applicable, they are coformulated as one unit dose comprising both the estrogen and the progestogen.

In certain embodiments, e.g., where a placebo is administered with the estrogen on days when progestogen is not administered, the estrogen and the placebo are formulated together. For oral administration, a given dose of each component, formulated together, can comprise one or more pills, tablets, capsules, or the like (i.e., unit doses). For example, an 8 mg dose of estriol and a placebo can be coformulated and administered as four capsules, each containing 2 mg estriol and a suitable amount of placebo.

When a given dose of any coformulation of estriol and progestogen (or placebo) involves administration of more than a single unit dose, e.g., four capsules, each containing 2 mg estriol and 0.0875 mg (or about 100 µg, or about 90 µg, or about 80 µg, or about 70 µg) norethindrone, the individual unit doses can be administered at essentially the same time, or they can be administered at different times on a given day, provided the entire daily dose is administered within a single day. For example, four capsules, each containing estriol and progestogen (or placebo) can be taken together essentially once a day, or they may be taken two at a time twice a day, or they may be taken one at a time four times a day. Additional schedules are contemplated by the invention, again provided the entire daily dose is administered within a single day. While it may be preferable that the subject follow the same schedule from one day to the next, such is not required, once again provided the entire daily dose is administered within a single day.

The term "subject" as used herein refers to a living mammal. In certain embodiments, "subject" is used interchangeably with the term "patient." In certain embodiments, the subject is a human. Preferably, the human subject is female, such as a woman.

In certain embodiments, the subject is pre-menopausal or peri-menopausal woman.

In certain embodiments, the subject is pre-menopausal woman.

In certain embodiments, the subject is peri-menopausal woman.

In certain embodiments, the subject as a post-menopausal woman.

In certain embodiments, the subject has relapsing-remitting MS.

In certain embodiments, the subject has secondary-progressive MS.

In certain embodiments, the subject has primary-progressive MS.

In certain embodiments, the subject has progressive-relapsing MS.

In certain embodiments, the subject has a mild form of any one of the foregoing subtypes of MS.

In certain embodiments, the subject has a moderate form of any one of the foregoing subtypes of MS.

In certain embodiments, the subject has an aggressive form of any one of the foregoing subtypes of MS.

In certain embodiments, the subject has clinically isolated syndrome.

Products Comprising an a Estrogen and a Progestogen

In some embodiments, the invention relates to a packaged pharmaceutical product, comprising a first region comprising a first series of doses of an estrogen, wherein each dose of the estrogen is associated with (e.g., adjacent or proximal to, or even co-located with) a dose of a progestogen; and a second region comprising a second series of doses of the estrogen that are not associated with doses of the progestogen. In such embodiments, the first region comprises both (i) a first series of doses of an estrogen and (ii) each dose of the progestogen with which the doses of estrogen are associated. In some embodiments, each dose of the estrogen in the second region is associated with a dose of placebo. In such embodiments, the second region comprises both (i) a second series of doses of an estrogen and (ii) each dose of the placebo with which the doses of estrogen are associated, such as in the manner in which the doses of estrogen in the first series are associated with doses of the progestogen.

The various doses of estrogen and progesterone may each be unit doses, such as tablets, capsules, caplets, or other oral dosage forms. Each dose of progestogen may be co-formulated with the dose of estrogen with which it is associated, e.g., as a combined unit dose.

The estrogen may be estradiol (E2), estriol (E3), estrone (E1), or a pharmaceutically acceptable salt of any of the foregoing, or any combination thereof. In preferred embodiments, the estrogen is estriol. In some embodiments, a dose of the estrogen comprises a dose equal or equivalent to about 200 µg to about 20 mg of estriol. For example, a dose of the estrogen may comprise a dose equal or equivalent to about 200 µg, 300 µg, 400 µg, 500 µg, 600 µg, 700 µg, 800 µg, 900 µg, 1 mg, 2 mg, 3 mg, 4 mg, 5 mg, 6 mg, 7 mg, 8 mg, 9 mg, 10 mg, 11 mg, 12 mg, 13 mg, 14 mg, 5 mg, 16 mg, 17 mg, 18 mg, 19 mg, or 20 mg. In preferred embodiments, a dose of the estrogen comprises a dose equal or equivalent to about 1 mg to about 10 mg of estriol. In more preferred embodiments, a dose of the estrogen comprises a dose equal or equivalent to about 8 mg of estriol. In some embodiments, a dose of the estrogen comprises 8 mg of estriol.

The progestogen may be a progestin. In some embodiments, the progestogen is progesterone, 17-hydroxyprogesterone, 5α-dihydroprogesterone, norethindrone (also known as norhisterone), norethindrone acetate (also known as norhisterone acetate), desogestrel, lecvonorgecstrel (Alesse®), medroxyprogesterone acetate (17α-hydroxy-6α-methylprogesterone acetate, Provera®), megestrol acetate (17α-acetoxy-6-dehydro-6-methylprogesterone), chlormadinone acetate, cyproterone acetate, norethynodrel (Enovid®), ethynodiol diacetate, norgestrel, gestodene, norgestimate, dienogest, drospirenone (Yasmin®), etonogestrel (Nexplanon®), nestorone, nomegestrol acetate, trimegestone, or tanaproget, or a pharmaceutically acceptable salt of any of the foregoing, or any combination thereof. In other embodiments, the progestogen is In preferred embodiments, the progestogen is norethindrone. In some embodiments, the progestogen comprises a dose equal or equivalent to about 70 µg to 7 mg of norethindrone. For example, a dose of the progestogen may comprise a dose equal or equivalent to about 100 µg, 200 µg, 300 µg, 400 µg, 500 µg, 600 µg, 700 µg, 800 µg, 900 µg, 1 mg, 2 mg, 3 mg, 4 mg, 5 mg, 6 mg, or 7 mg of norethindrone. In preferred embodiments, a dose of the progestogen comprises a dose equal or equivalent to about 100 µg to 1 mg of norethindrone. In more preferred embodiments, a dose of the progestogen comprises a dose equal or equivalent to about 700 µg of norethindrone. In some embodiments, a dose of the progestogen comprises 700 µg of norethindrone.

In some embodiments, each dose of the estrogen of the first series has a first color. In some embodiments, each dose of the estrogen of the second series has a second color. The first color and second color may be the same color. Alternatively, the first color and second color may be different colors. In some embodiments, each dose of the progestogen has a third color. In some embodiments, each dose of the placebo has a fourth color.

The product may comprise 28-365 doses of the estrogen. For example, the product may comprise 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 22, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, or 365 doses of the estrogen.

In some embodiments, the packaged pharmaceutical product comprises 5-84 doses of the progestogen. For example, the product may comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 doses of the progestogen In some embodiments, the first region comprises 5-21 doses each of the estrogen and the progestogen. For example, the first region may comprise 5, 6, 7, 8, 9, 10, 11, 12, 13, 14, 15, 16, 17, 18, 19, 20, or 21 doses of the estrogen and an equal number of doses of the progestogen. In preferred embodiments, the first region comprises 14 doses each of the estrogen and the progestogen. In such embodiments, the first region comprises 14 doses of the estrogen and 14 doses of the progestogen.

In some embodiments, the second region comprises 7-90 doses of the estrogen. For example, the second region may comprise 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 9) doses of the estrogen. In preferred embodiments, the second region comprises 14 or 70 doses of the estrogen. In more preferred embodiments, the second region comprises 70 doses of the estrogen.

In some embodiments, successive doses of the estrogen in each series are associated with successive days of an administration cycle, and the administration cycle consists of 28-365 consecutive calendar days. For example, the administration cycle may consist of 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 2104, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, or 365 consecutive calendar days. In certain embodiments, the administration cycle consists of 28 or 84 days. In preferred embodiments, the administration cycle consists of 84 days.

In some embodiments, the administration cycle consists of 4-52 weeks. For example, the administration cycle may consist of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks. In certain embodiments, the administration cycle consists of 4 or 12 weeks. In preferred embodiments, the administration cycle consists of 12 weeks.

In some embodiments, the administration cycle consists of 1-12 months. For example, the administration cycle may consist of 1, 2, 3, 4, 5, 6, 7, 8, 9, 10, 11, or 12 months. In certain embodiments, the administration cycle consists of 1 or 3 months. In preferred embodiments, the administration cycle consists of 3 months.

In some embodiments, the administration cycle consists of 1 year.

In some embodiments, the product comprises one or more first regions and one or more second regions, arranged in an alternating sequence, that together provide a number of doses of the estrogen equal to the number of days in the administration cycle. For example, the product may consist of one first region and one second region. Alternatively, the product may consist of two first regions and two second regions or three first regions and three second regions. In other embodiments, the product consists of four first regions and four second regions.

In certain embodiments, the administration cycle consists of 28 consecutive calendar days; the first region comprises 14 doses each of the estrogen and the progestogen; and the second region comprises 14 doses of the estrogen. In certain embodiments, the second region also comprises 14 doses of the placebo.

In other embodiments, the administration cycle consists of 84 consecutive calendar days; the first region comprises 14 doses each of the estrogen and the progestogen; and the second region comprises 70 doses of the estrogen. In certain embodiments, the second region also comprises 70 doses of the placebo.

The product may consist of one first series of doses and one second series of doses, and the first series of doses may be associated with days of the administration cycle that precede the days associated with the second series of doses. Alternatively, the product may consist of one first series of doses and one second series of doses, and the second series of doses may be associated with days of the administration cycle that precede the days associated with the first series of doses.

In some embodiments, the product comprises markings designating each dose for the day of the administration cycle associated with that dose. The markings may designate each dose with a day of the week or month. For example, the markings may designate the first dose in a series of doses with a first day of the administration cycle, and the markings may designate successive doses of the series with consecutive days of the week or month. In some embodiments, the markings designate the first dose of a series with a Sunday in the administration cycle. In other embodiments, the markings designate the first dose of the first or second series with a Monday, Tuesday, Wednesday, Thursday, Friday, or Saturday in the administration cycle.

In certain embodiments, the doses of estrogen are each individually enclosed in a chamber, optionally together with any associated dose of progestogen or placebo.

In some embodiments, the product comprises a first support structure, wherein the first region occupies a portion of the first support structure. In some embodiments, the product comprises two or more support structures. The second region may be divided among two or more of the support structures. In some embodiments, the first region and at least part of the second region occupy adjacent portions of the first support structure. For example, the second region may occupy a portion of the first support structure, an entire second support structure, and an entire third support structure. In other embodiments, the first region and second region are disposed on separate support structures. For example, the first region may be disposed on the first support structure and the second region may be disposed on one or more different support structures.

In certain embodiments, the support structures comprise at least one grid; the at least one grid comprises seven columns and at least four rows; the intersection of one row and one column defines a position that optionally comprises one or two chambers; and one dose of the estrogen occupies one chamber at a plurality of positions on the grid. In other embodiments, the support structures comprise at least one grid; the at least one grid comprises seven columns and at least four rows; the intersection of one row and one column defines a position that comprises one or two chambers; and one dose of the estrogen occupies one chamber at each position.

In some embodiments, the first support structure comprises a first grid; the first grid comprises 7 columns and 4-16 rows; each dose of estrogen from the first series occupies a chamber at consecutive positions on the first grid; and the remaining positions in the first grid each comprise one chamber that is occupied by one dose of estrogen from the second region. In preferred embodiments, the first grid comprises 4 or 16 rows. In more preferred embodiments, the first grid comprises 4 rows. Each column may correspond to a day of the week. For example, the first column may correspond to Sunday, the second column may correspond to Monday, the third column may correspond to Tuesday, the fourth column may correspond to Wednesday, the fifth column may correspond to Thursday, the sixth column may correspond to Friday, and the seventh column may correspond to Saturday. Similarly, each row may correspond to a week of the administration cycle. For example, the first row may correspond to the first week of the administration cycle, the second row may correspond to the second week of the administration cycle, the third row may correspond to the third week of the administration cycle, the fourth row may correspond to the fourth week of the administration cycle, the fifth row may correspond to the fifth week of the administration cycle, the sixth row may correspond to the sixth week of the administration cycle, the seventh row may correspond to the seventh week of the administration cycle, the eighth row may correspond to the eighth week of the administration cycle, the ninth row may correspond to the ninth week of the administration cycle, the tenth row may correspond to the tenth week of the administration cycle, the eleventh row may correspond to the eleventh week of the administration cycle, the twelfth row may correspond to the twelfth week of the administration cycle, and so forth.

In some embodiments, each dose of estrogen from the first series occupies one chamber at consecutive positions in the first two rows of the first grid. For example, in preferred embodiments, the first series of doses of estrogen comprises 14 doses of estrogen; the first grid comprises 7 columns and 4 rows; and each of the 14 doses of estrogen from the first series occupies one chamber in the 14 positions defined by the 7 columns and the first two rows of the first grid. Additionally, in preferred embodiments, the first region comprises 14 doses of progestogen, which are associated with each dose of estrogen from the first series; the first grid comprises 7 columns and 4 rows; and each of the 14 doses of progestogen from the first region occupies one chamber in the 14 positions defined by the 7 columns and first two rows of the first grid. Each dose of progestogen may occupy the same chamber as the dose of estrogen with which the dose of progestogen is associated. Alternatively, each dose of progestogen may occupy a separate chamber at the same position as the dose of estrogen with which the dose of progestogen is associated.

In some embodiments, the packaged pharmaceutical product comprises a second support structure that comprises a second grid, wherein the second grid comprises 7 columns and 4-8 rows; and one dose of estrogen from the second series occupies one chamber at each position of the second grid. In preferred embodiments, the second support structure comprises 7 columns and 4 rows. In such embodiments, the first support structure may be associated with the first four weeks of an administration cycle and the second support structure may be associated with the second four weeks of the administration cycle.

In some embodiments, the packaged pharmaceutical product comprises comprising a third support structure and a third grid, wherein; the third grid comprises 7 columns and 4 rows; and one dose of estrogen from the second series occupies one chamber at each position of the third grid. In preferred embodiments, the third support structure comprises 7 columns and 4 rows. In such embodiments, the first support structure may be associated with the first four weeks of an administration cycle, the second support structure may be associated with the second four weeks of the administration cycle, and the third support structure may be associated with the third four weeks of the administration cycle.

The first grid, second grid, or third grid may defined by Cartesian coordinates or polar coordinates. Each grid may be a Cartesian grid, regular grid, polar grid, rectilinear grid, curvilinear grid, or structured grid. For example, the first grid, second grid, or third grid may be a square grid, rectangular grid, or circular grid.

In some embodiments, each support structure is a blister pack, blister card, or push-through-pack. In some embodiments, the chambers are rupturable chambers. In certain embodiments, the product is configured to separately release each dose of estrogen, optionally together with any associated dose of progestogen or placebo.

Each dose of the estrogen may be provided in a separate chamber. Similarly, each dose of the progestogen may be provided in a separate chamber. Each dose of estrogen of the first series may be provided with its associated dose of progestogen in the same chamber. Alternatively, each dose of estrogen of the first series may be provided with its associated dose of progestogen in different chambers. In certain embodiments, the second region or regions are free of doses of progestogen.

In some embodiments, each dose of the placebo is provided in a separate chamber. Each dose of estrogen of the second series may be provided with its associated dose of placebo in the same chamber. Alternatively, each dose of estrogen of the second series may be provided with its associated dose of placebo in different chambers. In some embodiments, the first region or regions are free of doses of placebo.

In certain embodiments, the chambers are provided on a roll, a sheet, concentric rings, strips, or another pre-formed interconnection.

The doses may be adapted for oral administration. In certain embodiments, the doses of estrogen, progestogen, or placebo are provided in a tablet, pill, capsule, or gelcap.

Each dose of progestogen may be provided in a tablet, pill, capsule, or gelcap, wherein the tablet, pill, capsule, or gelcap contains the dose of estrogen with which the dose of progestogen is associated. For example, each tablet, pill, capsule, or gelcap may comprise a first compartment and a second compartment, wherein the first compartment contains one dose of progestogen and the second compartment contains the dose of estrogen with which the dose of progestogen is associated. Alternatively, each dose of progestogen may be provided in a tablet, pill, capsule, or gelcap, wherein the tablet, pill, capsule, or gelcap does not contain the dose of estrogen with which the dose of progestogen is associated.

In certain aspects, the invention relates to the use of a packaged pharmaceutical product in a therapeutic regimen for the treatment of a neurodegenerative disease, such as Alzheimer's disease, Parkinson's disease, multiple sclerosis, stroke, amyotrophic lateral sclerosis, cerebellar ataxia, frontotemporal dementia, prion disease, Huntington's Disease, cerebral ischaemia, idiopathic Morbus Parkinson, Parkinson syndrome. Morbus Alzheimers, cerebral dementia syndrome, infection-induced neurodegeneration disorders (e.g., AIDS-encephalopathy), Crutzfeld-Jakob disease, encephalopathies induced by rubiola and herpes viruses and borrelioses), metabolic-toxic neurodegenerative disorders (such as hepatic-, alcoholic-, hypoxic-, hypo- or hyperglycemically-induced encephalopathies), encephalopathies induced by solvents or pharmaceuticals, degenerative retina disorders, trauma-induced brain damage, trauma-induced bone marrow damage, cerebral hyperexcitability symptoms, cerebral hyperexcitability states (e.g., of varying origin, such as after the addition of and/or withdrawal of medicaments, toxins, noxae and drugs), neurodegenerative syndromes of the peripheral nervous system, peripheral nerve injury, and spinal cord injury. In certain preferred embodiments, the neurodegenerative disease is multiple sclerosis. In preferred embodiments, the patient is a woman. In some embodiments, the patient is a pre-menopausal or peri-menopausal woman. In other embodiments, the patient is a post-menopausal woman.

The various uses of the products disclosed herein can be for improving walking, vision, balance, cognition, or other symptoms in a subject, such as a subject with multiple sclerosis, and/or for improving PASAT, MS-COG (see Erlanger et al., J. Neuro. Sciences, 340, 2014, 123-129), symbol digital modalities test (SDMT), multiple sclerosis functional composite (MSFC), EDSS, or MSSS (multiple sclerosis severity score) scores in a subject, such as a subject with multiple sclerosis. In some embodiments, the products may be used to prevent, reduce the risk of developing, or delay the onset of relapsing-remitting multiple sclerosis (RRMS) in a subject who has clinically isolated syndrome (CIS).

In certain embodiments where the neurodegenerative disease is multiple sclerosis, the multiple sclerosis is relapsing-remitting multiple sclerosis. In certain embodiments, the multiple sclerosis is secondary-progressive multiple sclerosis. In certain embodiments, the multiple sclerosis is primary-progressive multiple sclerosis. In certain embodiments, the multiple sclerosis is progressive-relapsing multiple sclerosis. In certain embodiments, the subject has a mild form of any one of the foregoing subtypes of MS. In certain embodiments, the subject has a moderate form of any one of the foregoing subtypes of MS. In certain embodiments, the subject has an aggressive form of any one of the foregoing subtypes of MS. In certain embodiments, the multiple sclerosis is, more accurately, so-called clinically isolated syndrome (CIS).

While the therapeutic regimens disclosed herein are typically efficacious when administered without additional therapeutics, in certain embodiments, they may be used in conjunction with treatment with an immunotherapeutic agent (i.e., besides the estrogen and progestogen). That is, in certain embodiments, the packaged pharmaceuticals are used to treat a subject who is also receiving a third agent useful in the treatment of MS. Such agents useful in the treatment of MS are, in general, immunotherapeutic agents. At least in connection with MS, such agents are sometimes referred to as disease-modifying therapies or disease-modifying therapeutics (DMTs).

The term "immunotherapeutic agent" as used herein refers to a compound with an objectively measurable effect on at least one aspect of the immune system or an immune response. In certain embodiments, the immunotherapeutic agent is immunosuppressive, i.e., it exerts an objectively measurable inhibitory effect on at least one aspect of the immune system or an immune response. In certain embodiments, the immunotherapeutic agent is anti-inflammatory. In certain embodiments, the immunotherapeutic agent is a small molecule (molecular weight less than or equal to about 1.5 kDa) pharmaceutical compound or composition. In certain embodiments, the immunotherapeutic agent is a biological compound or composition, e.g., an antibody, peptide, nucleic acid, etc.

In certain embodiments, the immunotherapeutic agent is not an estrogen. In certain embodiments, the immunotherapeutic agent is not a progestogen. Preferably, the immunotherapeutic agent is neither an estrogen nor a progestogen.

In certain embodiments, the immunotherapeutic agent is selected from dimethyl fumarate (Tecfidera®; BG-12), fingolimod (Gilenya®), glatiramer acetate (Copaxone®), interferon beta-1a (Avonex® or Rebif®), interferon beta-1b (Betaseron® or Extavia®), mitoxantrone (Novantrone®), natalizumab (Tysabri®), and teriflunomide (Aubagio®), mycophenolate mofetil, paclitaxel, cyclosporine, corticosteroids (e.g., prednisone, methylprenisolone), azathioprine, cyclophosphamide, methotrexate, cladribine, 4-aminopyridine, and tizanidine. In certain embodiments, the immunotherapeutic agent is selected from dimethyl fumarate (Tecfidera®; BG-12), fingolimod (Gilenya®), glatiramer acetate (Copaxone®), interferon beta-1a (Avonex® or Rebif®), interferon beta-1b (Betaseron® or Extavia®), mitoxantrone (Novantrone®), natalizumab (Tysabri®), and teriflunomide (Aubagio®).

In certain embodiments, the immunotherapeutic agent is dimethyl fumarate (Tecfidera®; BG-12), which may be administered in an amount from about 220 mg to about 260 mg per day, such as about 220 mg, 240 mg, or 260 mg per day. In certain embodiments, the immunotherapeutic agent is fingolimod (Gilenya®), which may be administered in an amount from about 0.25 mg to about 0.75 mg per day, such as about 0.25 mg, 0.50 mg, or 0.75 mg per day. In certain embodiments, the immunotherapeutic agent is glatiramer acetate (Copaxone®). In certain embodiments, the immunotherapeutic agent is interferon beta-1a (Avonex® or Rebif®). In certain embodiments, the immunotherapeutic agent is interferon beta-1b (Betaseron® or Extavia®). In certain embodiments, the immunotherapeutic agent is mitoxantrone (Novantrone®). In certain embodiments, the immunotherapeutic agent is natalizumab (Tysabri®). In certain embodiments, the immunotherapeutic agent is teriflunomide (Aubagio®), which may be administered in an amount from about 7 mg to about 14 mg per day, such as about 7 mg, 10 mg, or 14 mg per day.

In certain embodiments, the subject is already receiving a disease-modifying therapeutic. In this circumstance, the subject can continue to receive the disease-modifying therapeutic while taking the estrogen, with and without the progestogen. Significantly, however, the dose of the disease-modifying therapeutic may be decreased when used in combination with the estrogen, with and without the progestogen. For example, a current standard dose for glatiramer acetate (Copaxone®) is 40 mg subcutaneously (s.c.) three times a week, or 20 mg s.c. daily. In conjunction with estrogen and progestogen in accordance with the invention, the dose for glatiramer acetate (Copaxone®) may be reduced by up to 50 percent or more, e.g., to 20 mg s.c. three times a week.

As another example, a current standard dose for fingolimod (Gilenya®) is 0.5 mg by mouth (p.o.) daily. In conjunction with estrogen and progestogen in accordance with the invention, the dose for fingolimod (Gilenya®) may be reduced by up to 50 percent or more, e.g., to 0.25 mg p.o. daily.

As another example, a current standard dose for dimethyl fumarate (Tecfidera®) is 240 mg p.o. daily. In conjunction with estrogen and progestogen in accordance with the invention, the dose for dimethyl fumarate (Tecfidera®) may be reduced by up to 50 percent or more, e.g., to 120 mg p.o. daily.

As yet another example, a current standard dose for interferon beta-1a (Avonex® or Rebif®) is 30 Mg intramuscularly (i.m.) weekly (Avonex®) or 44 µg s.c. three days a week (Rebif®). In conjunction with estrogen and progestogen in accordance with the invention, the dose for Avonex® may be reduced to 15 µg i.m. weekly, and the dose for Rebif® may be reduced to 22 µg s.c. three days a week.

As yet another example, a current standard dose for interferon beta-1b (Betaseron® or Extavia®) is 0.25 mg s.c. every other day (Betaseron® or Extavia®). In conjunction with estrogen and progestogen in accordance with the invention, the dose for interferon beta-1b (Betaseron® or Extavia®) may be reduced to 0.125 mg s.c. every other day.

In certain embodiments, the subject is receiving an immunotherapeutic agent and experiencing a relapse or progression of the multiple sclerosis. For example, a subject may experience a relapse or progression while on a maintenance dose of a DMT. Such subject can then begin concurrent treatment with estrogen in accordance with any of the various packaged pharmaceutical products disclosed herein, e.g., to reduce the frequency and/or severity of relapses or to slow progression of the disease (e.g., as determined by assessment of one or more of walking, vision, balance, cognition, or other symptoms of the condition). Similarly, various uses of the products disclosed herein are for improving walking, vision, balance, cognition, or other symptoms in a subject, such as a subject with multiple sclerosis, and/or for improving EDSS or MSSS scores in a subject, such as a subject with multiple sclerosis. In some embodiments, the products may be used to prevent, reduce the risk of developing, or delay the onset of relapsing-remitting multiple sclerosis (RRMS) in a subject who has clinically isolated syndrome (CIS).

In certain embodiments, the subject is receiving an immunotherapeutic agent and experiencing a relapse of the multiple sclerosis. For example, a subject may experience a relapse while on a maintenance dose of a DMT. Such subject can then begin concurrent treatment with estrogen in accordance with a method of the present invention, e.g., to reduce the frequency and/or severity of relapses.

In certain embodiments, the subject is receiving an immunotherapeutic agent selected from interferon-beta 1a, interferon-beta 1b, glatiramer acetate, natalizumab, mitoxantrone, fingolimod, teriflunomide, and dimethyl fumarate during a ramp-up period for dose of the immunotherapeutic agent, e.g., the patient begins receiving the immunotherapeutic and the estrogen therapy at the same time or at about the same time (such as for patients who have not previously received treatments for their disease). Advantageously, estrogen induces a rapid onset of therapeutic effect on MS, while commonly an immunotherapeutic agent such as interferon-beta 1a, interferon-beta 1b, glatiramer acetate, natalizumab, mitoxantrone, fingolimod, teriflunomide, or dimethyl fumarate may take weeks to months to induce observable improvements on some or all symptoms.

Kit Comprising an Estrogen and a Progestogen

In certain aspects, the invention relates to a kit for providing estrogen and a progestogen as disclosed herein, such as a kit having one container holding doses of estrogen and a second container holding doses of a progestogen, together with instructions for administering them in accordance with an administration cycle as disclosed herein. For example, the kit may comprise a container comprising 84 doses of an estrogen, a container comprising 14 doses of a progestogen, and instructions for ingesting the doses of estrogen and progestogen, wherein the instructions direct a subject to ingest one dose of estrogen and one dose of progestogen daily for 14 consecutive days, and after 14 consecutive days, the instructions direct the subject to ingest one dose of estrogen daily for 70 consecutive days.

Methods of Using Products Comprising an Estrogen and a Progestogen

In certain aspects, the invention relates to a method of using a packaged pharmaceutical product, comprising ingesting one dose of an estrogen and one dose of a progestogen daily from a first region of the product, and when the doses in the first region are exhausted, ingesting one dose of estrogen daily from a second region of the product. In some embodiments, when the doses in the first region are exhausted, the method comprises ingesting one dose of the placebo daily from the second region of the product with each dose of the estrogen from the second series with which the dose of the placebo is associated.

Ingesting one dose of an estrogen and one dose of a progestogen daily from a first region of the product may comprise ingesting one dose of an estrogen and one dose of a progestogen daily for 5-21 consecutive days. For example, ingesting one dose of an estrogen and one dose of a progestogen daily from a first region of the product may comprise ingesting one dose of an estrogen and one dose of a progestogen daily for 5, 6, 7, 8, 9, 10, 11, 12, 13, 14, 15, 16, 17, 18, 19, 20, or 21 consecutive days, preferably 14 days.

In some embodiments, ingesting one dose of the estrogen daily from a second region of the product comprises ingesting one dose of an estrogen daily for 7-90 days. For example, ingesting one dose of an estrogen daily from a second region of the product may comprise ingesting one dose of an estrogen daily for 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 consecutive days, preferably 70 days.

In some embodiments, ingesting one dose of the placebo daily from a second region of the product comprises ingesting one dose of the placebo daily for 7-90 days, preferably 70 days.

In certain embodiments, successive doses of the estrogen in each series are ingested on successive days of an administration cycle. Each dose of estrogen may be ingested on the day that an administration cycle designates for that dose to be ingested. The product may designate each dose of estrogen with a number, and successive doses of estrogen may be ingested on days that correspond to consecutive numbers.

In some embodiments, the product designates each dose of estrogen with a day of the week or month, and successive doses of estrogen are ingested on days that correspond to successive days of the week or month.

In certain embodiments, the product comprises a blister pack, blister card, or push-through-pack that contains the doses of the estrogen, progestogen, or placebo, and in such embodiments, the method preferably comprises removing one dose of the estrogen, progestogen, or placebo from the blister pack, blister card, or push-through-pack prior to ingesting the dose.

In some embodiments, the product comprises rupturable chambers that contain the doses of the estrogen, progestogen, or placebo, and the method comprises rupturing the chamber containing a dose of the estrogen, progestogen, or placebo prior to ingesting the dose.

In certain embodiments, ingesting a dose consists of ingesting a unit dose.

In preferred embodiments, the method is performed by a woman, such as a pre-menopausal, post-menopausal, or peri-menopausal woman.

In certain embodiments, ingesting each dose of the estrogen comprises ingestion each dose of the estrogen at about the same time every day. The first dose of estrogen and the first dose of progestogen from the first region may be ingested on a Sunday. Similarly, the first dose of estrogen from the second region may be ingested on a Sunday.

In some embodiments, if one dose is skipped on one day, then two doses are ingested on the following day. Similarly, if two doses are skipped on two consecutive days, then two doses may be ingested on each of the following two days.

Products for Gradually Terminating Estrogen Therapy

In some aspects, the invention relates to a packaged pharmaceutical product comprising a first region comprising a first series of doses of an estrogen, wherein each dose of the estrogen comprises a dose equal or equivalent to about 4 mg of estriol, and a second region comprising a second series of doses of the estrogen, wherein each dose of the estrogen comprises a dose equal or equivalent to about 2 mg of estriol. The estrogen may be estradiol (E2), estriol (E3), estrone (E1), or a pharmaceutically acceptable salt of any of the foregoing, or any combination thereof. In preferred embodiments, the estrogen is estriol.

In some embodiments, each dose of the estrogen from the first series of doses of estrogen has a first color. In some embodiments, each dose of the estrogen from the second series of doses of estrogen has a second color.

The product may comprise 28 doses of the estrogen. The first region may comprise 14 doses of the estrogen, and the second region may comprise 14 doses of the estrogen.

In certain embodiments, successive doses of the estrogen in each series are associated with successive days of an administration cycle, wherein the administration cycle consists of about 28 consecutive calendar days. In certain embodiments, the administration cycle consists of 4 weeks. In some embodiments, the administration cycle consists of 1 month.

In some embodiments, the administration cycle consists of 28 consecutive calendar days; the first series comprises 14 doses of the estrogen; and the second series comprises 14 doses of the estrogen.

The product may consist of one first series of doses and one second series of doses, and the first series of doses may be associated with days of the administration cycle that precede the days associated with the second series of doses.

The package may further comprise markings designating each dose for the day of the administration cycle associated with that dose. For example, the markings may designate each dose with a day of the week or month. The first dose of the first series of estrogen may be designated with a Sunday. Similarly, the first dose of the second series of estrogen may be designated with a Sunday.

The doses of estrogen may each be individually enclosed in a chamber.

In some embodiments, the invention further comprises a support structure, wherein the first region and the second region occupy portions of the support structure. The support structure may be a blister pack, blister card, or push-through-pack.

In some embodiments, the support structure comprises a grid; the grid comprises seven columns and four rows; the intersection of one row and one column defines a position that comprises one chamber; and one dose of the estrogen occupies one chamber at each position. In preferred embodiments, each dose of estrogen from the first series occupies one chamber in the first two rows of the grid; and the remaining positions in the grid each comprise one chamber that is occupied by one dose of estrogen from the second region.

The first grid, second grid, or third grid may defined by Cartesian coordinates or polar coordinates. Each grid may be a Cartesian grid, regular grid, rectilinear grid, curvilinear grid, or structured grid. For example, the first grid, second grid, or third grid may be a square grid, rectangular grid, or circular grid.

In some embodiments, the package is configured to separately release each dose of estrogen. In some embodiments, the chambers are rupturable chambers. Each dose of the estrogen may be provided in a separate chamber. The chambers may be provided on a roll, a sheet, concentric rings, strips, or another pre-formed interconnection.

In some embodiments, the doses of estrogen are adapted for oral administration. The doses of estrogen may be provided as tablets, pills, capsules, or gelcaps. Each dose of estrogen may be a unit dose.

In certain aspects, the invention relates to the use of the packaged pharmaceutical product in a therapeutic regimen for the treatment of a patient suffering from a neurodegenerative disease, such as multiple sclerosis. Preferably, the patient is a woman, such as a pre-menopausal or peri-menopausal woman. Alternatively, the patient may be a post-menopausal woman.

Method for Gradually Terminating Estrogen Therapy

In certain aspects, the invention relates to a method of using a packaged pharmaceutical product comprising ingesting one dose of an estrogen daily from a first region of the product, and when the doses from the first region are exhausted, ingesting one dose of the estrogen daily from a second region of the product.

In some embodiments, ingesting one dose of an estrogen daily from a first region of the product comprises ingesting one dose of the estrogen daily for about 14 consecutive days. Similarly, in some embodiments, ingesting one dose of an estrogen daily from a second region of the product comprises ingesting one dose of the estrogen daily for 14 consecutive days.

In certain embodiments, successive doses of the estrogen in each series are ingested on successive days of an administration cycle, and the administration cycle is 28 days long.

Each dose of estrogen may be ingested on the day that an administration cycle designates for that dose to be ingested. The product may designate each dose of estrogen with a number, and successive doses of estrogen may be ingested on days that correspond to consecutive numbers. Similarly, the product may designate each dose of estrogen with a day of the week or month, and successive doses of estrogen may be ingested on days that correspond to successive days of the week or month.

In certain embodiments, the product comprises a blister pack, blister card, or push-through-pack that contains the doses of the estrogen, and the method comprises removing one dose of the estrogen from the blister pack, blister card, or push-through-pack prior to ingesting the dose.

In some embodiments, the product comprises rupturable chambers that contain the doses of the estrogen, and the method comprises rupturing the chamber containing a dose of the estrogen prior to ingesting the dose.

In certain embodiments, ingesting a dose of estrogen consists of ingesting a unit dose.

Preferably, the method is performed by a woman, such as a pre-menopausal, post-menopausal, or peri-menopausal woman.

In certain embodiments, ingesting each dose of the estrogen comprises ingesting each dose of the estrogen at about the same time every day. The first dose of estrogen the first region may be ingested on a Sunday. Similarly, the first dose of estrogen from the second region may be ingested on a Sunday.

In some embodiments, if one dose is skipped on one day, then two doses are ingested on the following day. Similarly, if two doses are skipped on two consecutive days, then two doses may be ingested on each of the following two days.

Having now described the present invention in detail, the same will be more clearly understood by reference to the following examples, which are included herewith for purposes of illustration only and are not intended to be limiting of the invention.

EXAMPLES

Example 1—Use of Copaxone® and Estriol for the Treatment of Multiple Sclerosis

This example describes a randomized, double-blind, placebo-controlled human clinical trial for the treatment of multiple sclerosis using Copaxone® and estriol.

Enrollment Criteria

Eligible patients were female, between ages 18 and 50, had active relapsing disease, and had an Expanded Disability Status Scale (EDSS) score between 0 and 4.5. Women who were pregnant, breastfeeding, taking hormone replacement therapy, or taking oral contraceptives were excluded from the trial.

Study Conduct and Monitoring Schedule

Patients were randomized to Copaxone® (glatiramer acetate) injections (20 mg/day) and oral estriol (8 mg/day) or to Copaxone® injections and placebo for a 24-month treatment duration. Gynecologists examined the patients before, during, and after the study. Each patient was examined at three- to six-month intervals during the trial. Patients also underwent mammograms before and after the study. In addition, at baseline, three months, six months, 12 months, 18 months, and 24 months, the investigators measured participants' estriol levels, and assessed for MS relapses and MS-related disabilities.

A total of 82 patients received Copaxone® plus estriol, and 76 patients received Copaxone® plus placebo. Baseline characteristics were similar in both patient groups. Participants' mean age at entry was approximately 38, and their mean EDSS score at entry was 2.2. Estriol levels in serum were in a mid-pregnancy range in the estriol-treated group. To ensure breast and uterus safety, every three months the patients took norethindrone 0.7 mg once a day for 14 days. This hormone regimen was found to be safe and well tolerated with regard to serious adverse events, adverse events, general exams, blood chemistries, and hematological studies, as well as for gynecological outcomes (see Table 1).

TABLE 1

Safety and Tolerability Data

| Patient Group[a] | Uterine fibroids on ultrasound | Uterine endometrial thickness > 8 mm on ultrasound | Uterine endometrial biopsies | Breast - Fibrocystic breast disease on clinical exam | Mammograms |
|---|---|---|---|---|---|
| Placebo | 8 subjects | 27 subjects with 41 exams | 6 subjects with 10 exams (no abnormal proliferation) | 4 subjects | No breast cancer |
| Estriol | 8 subjects | 24 subjects with 32 exams | 9 subjects with 11 exams (no abnormal proliferation) | 5 subjects | |

[a]Patients received Copaxone ® with either estriol or placebo

Primary Outcome Measure

The primary outcome measure for disease efficacy was annualized relapse rate.

Figure 1:
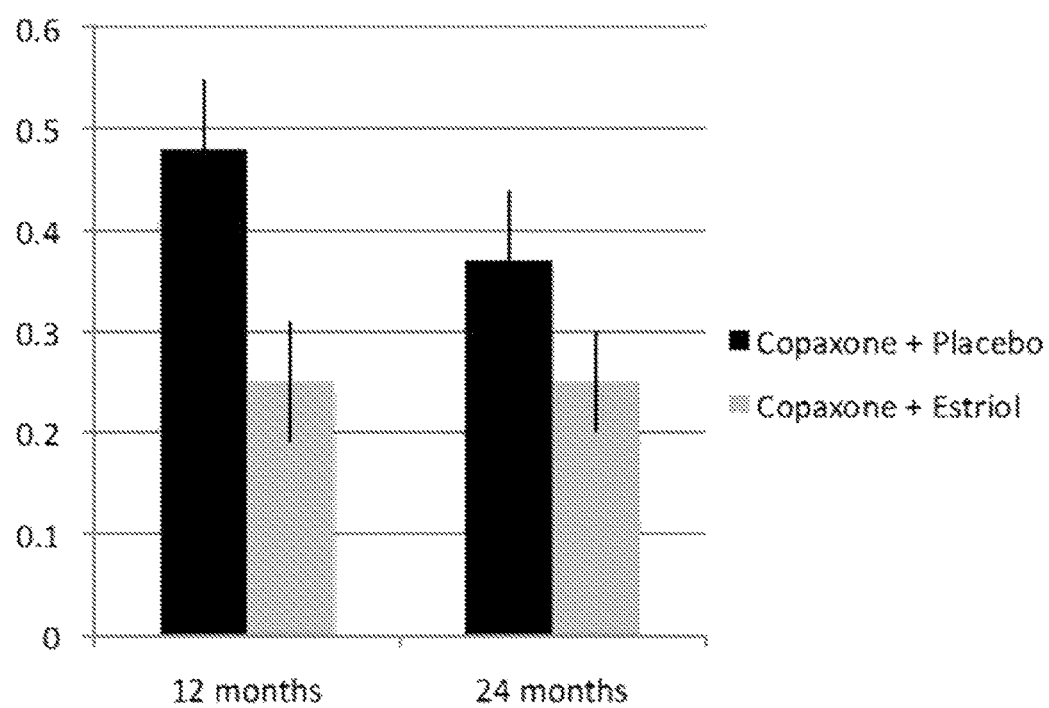
FIG. 1 is a bar graph depicting annualized relapse rates with Copaxone plus estriol treatment as compared to Copaxone plus estriol placebo treatment.

While most Phase II trials used surrogates or biomarkers as the primary outcome, the trial focused on an outcome measure acceptable for approval by the FDA. Since this was a Phase II trial, it was powered to reduce relapses by one third more in the Copaxone® plus estriol group as compared to the Copaxone® plus placebo group, with a targeted p value of p=0.10 at the end of study which was 24 months. As shown in FIG. 1, after 24 months of treatment the primary outcome measure was attained by reducing relapse rates by 32% (p=0.11) in the Copaxone® plus estriol group as compared to the Copaxone® plus placebo group. Surprisingly, after only 12 months of treatment, the relapse rate was reduced by 47% (p=0.02) in the Copaxone® plus estriol group as compared to the Copaxone® plus placebo group, see FIG. 1. Thus, in addition to finding that Copaxone® plus estriol treatment had significant benefit in reducing the frequency of relapses over 24 months, the combination treatment also had a more rapid onset of action as compared to Copaxone® plus placebo.

These results were surprising given that estriol treatment was not compared to a true placebo, but rather was tested in combination with standard-of-care therapy (Copaxone®). Since anti-inflammatory drugs the FDA has approved have so far required much larger sample sizes to show a significant reduction in relapse rates, even as compared to a true placebo, the results of the study adding estriol to Copaxone® suggest a novel mechanism of action, a mechanism never before observed in MS.

Cognitive Disability Assessment

Figure 2:
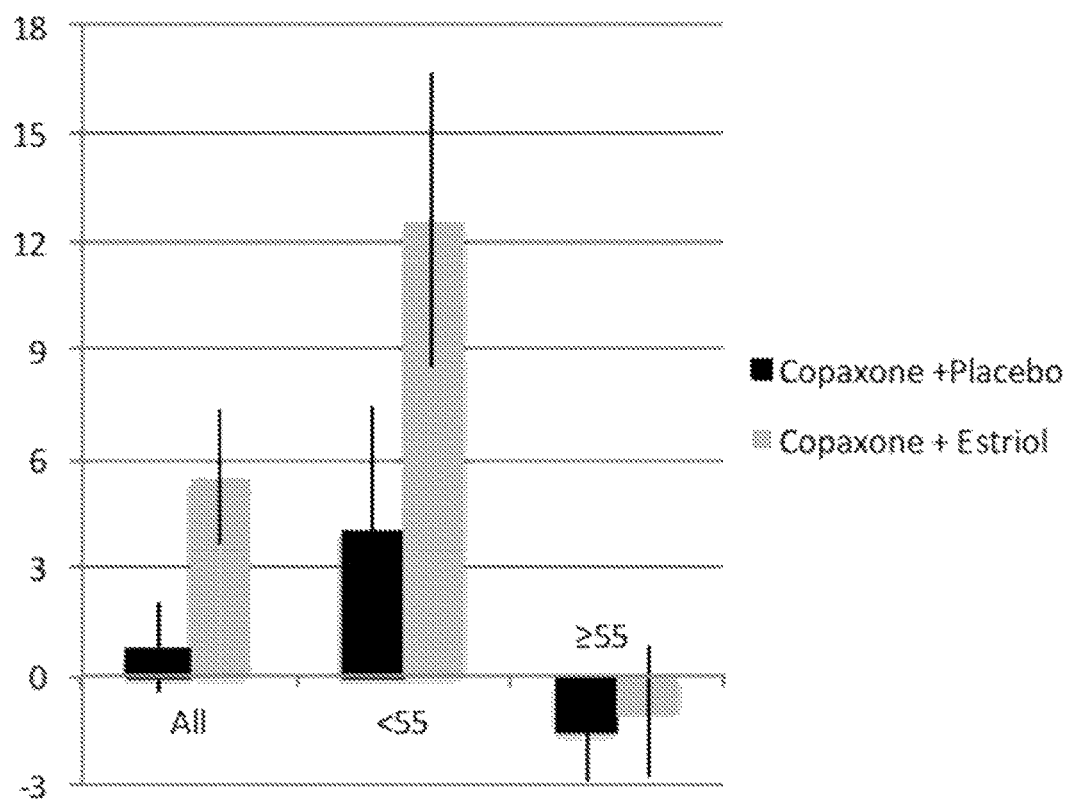
FIG. 2 is a bar graph depicting Paced Serial Addition Test (PASAT) cognitive test scores for all subjects (All), subjects with baseline scores of less than 55/60 (<55), and subjects with baseline scores greater than or equal to 55/60 (≥55). Comparison is made between treatment groups receiving Copaxone plus estriol or Copaxone plus estriol placebo. Data are expressed as percent change from baseline in each treatment group.

The effect of treatment was assessed on cognitive disability with a test for processing speed that has been extensively used in MS, the Paced Auditory Serial Addition Test (PASAT). A perfect score is 60, with scores lower than 55 indicating disability. By 12 months of treatment, scores on the PASAT improved by approximately 6% (i.e., 3 points), compared with scores at baseline, among patients receiving Copaxone® plus estriol (p=0.03). The change largely resulted from a 12% improvement (i.e., 6 points) among participants with cognitive disability prior to treatment as reflected in scores of less than 55 at baseline (of a maximum of 60), see FIG. 2. After 12 months of treatment, patients receiving Copaxone® plus estriol continued to have high PASAT scores to the end of study at month 24, while participants receiving placebo began to show improved PASAT scores by month 24. Notably, a change of six or more points in tests of processing speed in MS is considered to be clinically significant. Further, Copaxone® plus estriol treatment improved function in those with significant cognitive disability, rather than merely slowing cognitive decline. This represents repair of disability, not merely prevention of worsening.

Figure 3:
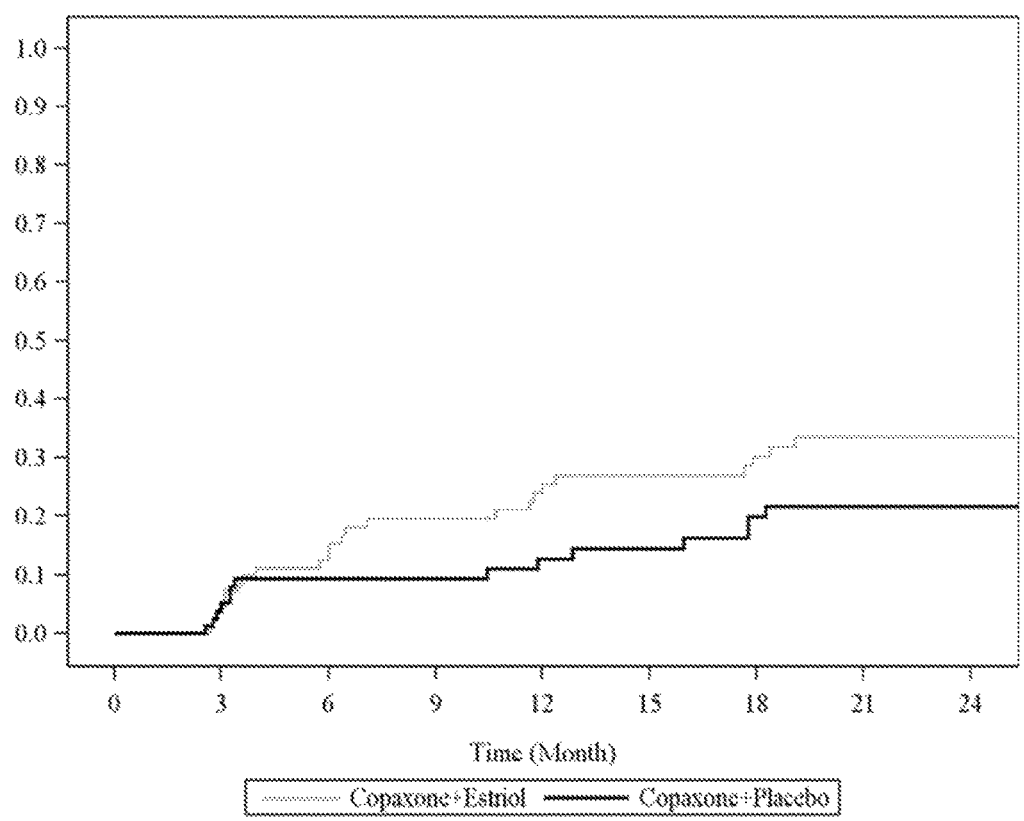
FIG. 3 is a graph depicting the proportion of all subjects who had sustained improvement of 3 points in PASAT scores for 6 months. Comparison is made between treatment groups receiving Copaxone plus estriol (upper curve) or Copaxone plus estriol placebo (lower curve).

Next it was shown that the improvement in PASAT cognitive test scores was sustained when subjects were followed for the entire 24 month period, p=0.02 (FIG. 3).

In addition, the beneficial effects of estriol treatment on cognitive function were shown using another cognitive test, the 7/24 spatial recall test (for spatial memory). While initial encoding of information did not differ between groups, the number of subjects with perfect scores for immediate recall (p=0.006) and delayed recall (p=0.04) was higher in the Copaxone® plus estriol treated group as compared to the Copaxone®) plus placebo treated group over the entire 24 month treatment duration. Such rapid and potent effects on cognition observed in the Copaxone plus estriol group as compared to the Copaxone plus placebo group were surprising and point to a novel effect on cognitive disability unseen previously with other FDA-approved MS drugs.

Ambulatory Assessment

Figure 4:
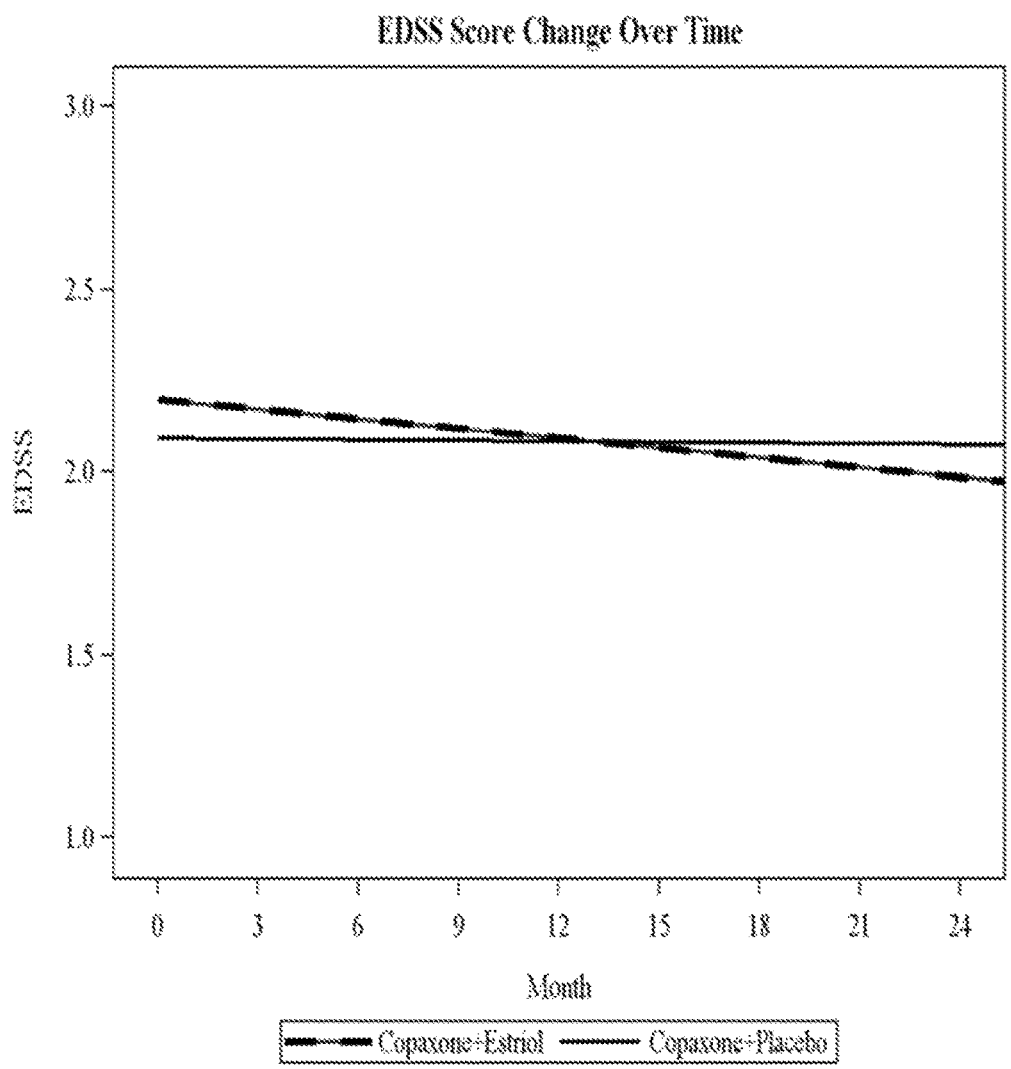
FIG. 4 is a graph depicting Expanded Disability Status Scale (EDSS) scores over 24 months for treatment groups receiving Copaxone plus estriol (slope=−4.11, p=0.06) or Copaxone plus estriol placebo (slope=−0.01, p=0.90).

The Expanded Disability Status Scale (EDSS) is a standard composite disability score used in MS trials. Higher scores indicate worse disability. This composite covers a variety of disabilities (including ambulation, vision, cognition, coordination, etc.), but scoring is not linear, and the composite score is understood to be principally an indicator of the level of disability in ambulation. While there was no change in the EDSS scores for the Copaxone® plus placebo treatment group, the Copaxone® plus estriol treatment group showed a significant decrease (i.e., improvement) in this disability score (FIG. 4). Further, the probability of EDSS progression (as defined by an increase in EDSS of 1 point for over 6 months) was 19% lower in the Copaxone® plus estriol group, while the probability of EDSS improvement (as defined by a decrease in EDSS of 1 point for over 6 months) was 23% higher in the Copaxone® plus estriol group.

Another clinical disability measure with treatment effects was the timed 25-foot walk test. This test measures how many seconds it takes to walk 25 feet, with higher scores indicating worse disability. The walk time was significantly increased in the Copaxone® plus placebo group (p=0.03), while it was slightly decreased in the Copaxone® plus estriol group, together resulting in a significant between-group difference (p=0.02). Together these data show a gradual worsening in walking times in the Copaxone® plus placebo treated group, which did not occur in the Copaxone® plus estriol treated group. This beneficial effect of estriol treatment on 25 foot walking times is consistent with the beneficial effect of estriol treatment on EDSS scores since the latter is weighted toward being an indicator of ambulation.

Figure 5A:
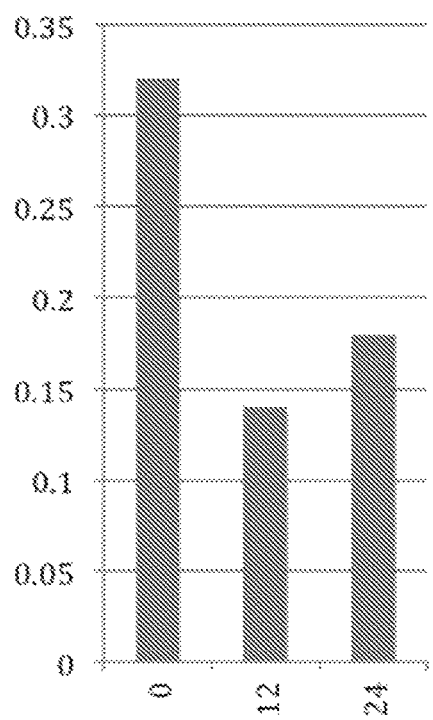
FIG. 5 shows that the number of subjects with brain MRIs that had enhancing lesions at 12 months was reduced by 56% with Copaxone+estriol treatment (A), while they were reduced by only 22% with Copaxone+placebo treatment (M), each as compared to month 0 baseline.
Figure 5B:
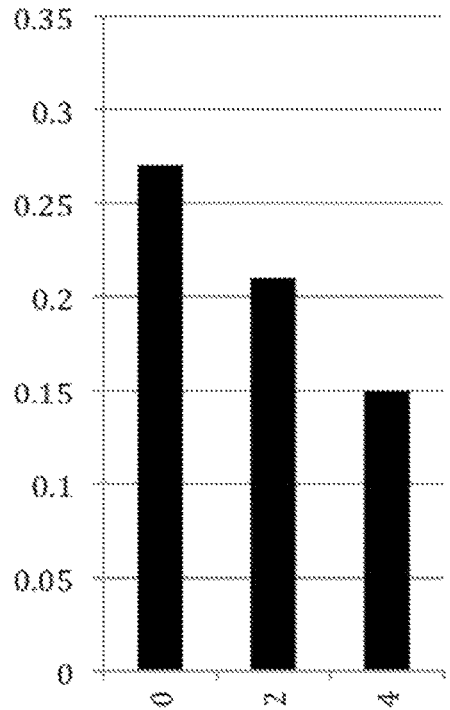

Brain MRI is used extensively in MS as a surrogate marker for clinical effects. Brain white matter gadolinium enhancing lesions are a biomarker for relapses. We found that the number of subjects with brain MRI scans that were positive for enhancing lesions were reduced by 56% at month 12 in the Copaxone plus estriol treatment group vs. by 22% in the Copaxone plus placebo treatment group (p=0.14). This effect is consistent with the observation that the Copaxone plus estriol group demonstrated a more rapid onset of action in reducing relapse rates as compared to the Copaxone plus placebo group (FIG. 5A, B).

INCORPORATION BY REFERENCE

All patents, published patent applications, and other publications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

The invention claimed is:

1. A packaged pharmaceutical product, comprising:
a first region comprising a first series of doses of estriol, wherein each dose of the estriol is co-located with a dose of a progestogen; and
a second region comprising a second series of doses of the estriol that are not co-located with doses of the progestogen; wherein
each dose of estriol comprises about 8 mg of estriol.

2. The packaged pharmaceutical product of claim 1, wherein each dose of the estriol in the second region is co-located with a dose of placebo.

3. The packaged pharmaceutical product of claim 1, wherein each dose of progestogen is co-formulated with a dose of estriol.

4. The packaged pharmaceutical product of claim 1, wherein the progestogen is a progestin.

5. The packaged pharmaceutical product of claim 1, wherein the progestogen is progesterone, 17-hydroxyprogesterone, 5α-dihydroprogesterone, norethindrone, norethindrone acetate, desogestrel, levonorgestrel, medroxyprogesterone acetate, megestrol, chlormadinone acetate, cyproterone acetate, norethynodrel, ethynodiol diacetate, norgestrel, gestodene, norgestimate, dienogest, drospirenone, etonogestrel, nestorone, nomegestrol acetate, trimegestone, tanaproget, or a pharmaceutically acceptable salt of any of the foregoing, or any combination thereof.

6. The packaged pharmaceutical product of claim 1, wherein a dose of the progestogen comprises a dose equal or equivalent to about 100 μg to 1 mg of norethindrone.

7. The packaged pharmaceutical product of claim 6, wherein a dose of the progestogen comprises a dose equal or equivalent to about 700 μg of norethindrone.

8. The packaged pharmaceutical product of claim 1, wherein successive doses of the estriol in each series are associated with successive days of an administration cycle, and the administration cycle consists of 28-365 consecutive calendar days.

9. The packaged pharmaceutical product of claim 8, wherein the administration cycle consists of 4 weeks.

10. The packaged pharmaceutical product of claim 8, wherein the administration cycle consists of 1 month.

11. The packaged pharmaceutical product of claim 1, wherein:
the administration cycle consists of 84 consecutive calendar days;
the first region comprises 14 doses each of the estriol and the progestogen; and
the second region comprises 70 doses of the estriol.

12. The packaged pharmaceutical product of claim 11, wherein the second region comprises a number of doses of the placebo that is equal to the number of doses of the estriol within the second region.

13. The packaged pharmaceutical product of claim 2, wherein the doses are adapted for oral administration.

14. The packaged pharmaceutical product of claim 13, wherein the doses of estriol, progestogen, or placebo are provided in a tablet, pill, capsule, or gelcap.

15. A method of treating multiple sclerosis using a packaged pharmaceutical product, the method comprising:
ingesting one dose of an estriol and one dose of a progestogen daily from a first region of the product; and
when the doses in the first region are exhausted, ingesting one dose of estriol daily from a second region of the product;
wherein the product comprises:
a first region comprising a first series of doses of an estriol, wherein each dose of the estriol is co-located with a dose of a progestogen; and
a second region comprising a second series of doses of the estriol that are not co-located with doses of the progestogen; wherein
each dose of estriol comprises about 8 mg of estriol.

16. The packaged pharmaceutical product of claim 11, wherein the dose of the progestogen comprises a dose equal or equivalent to about 100 μg to 1 mg of norethindrone.

17. The packaged pharmaceutical product of claim 11, wherein the dose of the progestogen comprises a dose equal or equivalent to about 700 μg of norethindrone.

18. The method of claim 15, wherein the first series of doses comprises 14 doses each of the estriol and the progestogen; and the second region comprises 70 doses of the estriol.

19. The method of claim 15, wherein the dose of the progestogen comprises a dose equal or equivalent to about 700 μg of norethindrone.

20. The method of claim 18, wherein the dose of the progestogen comprises a dose equal or equivalent to about 700 μg of norethindrone.

* * * * *